(12) United States Patent
Binkert

(10) Patent No.: US 9,017,363 B2
(45) Date of Patent: Apr. 28, 2015

(54) BLOOD FILTER

(75) Inventor: Christoph Andreas Binkert, Winterthur (CH)

(73) Assignee: Cook Medical Technologies LLC, Bloomington, IN (US)

( * ) Notice: Subject to any disclaimer, the term of this patent is extended or adjusted under 35 U.S.C. 154(b) by 815 days.

(21) Appl. No.: 13/062,434

(22) PCT Filed: Sep. 5, 2008

(86) PCT No.: PCT/EP2008/061819
§ 371 (c)(1),
(2), (4) Date: May 18, 2011

(87) PCT Pub. No.: WO2010/025775
PCT Pub. Date: Mar. 11, 2010

(65) Prior Publication Data
US 2011/0213404 A1 Sep. 1, 2011

(51) Int. Cl.
*A61M 29/00* (2006.01)
*A61F 2/01* (2006.01)
*A61F 2/86* (2013.01)

(52) U.S. Cl.
CPC ... *A61F 2/01* (2013.01); *A61F 2/86* (2013.01); *A61F 2210/0004* (2013.01); *A61F 2250/003* (2013.01); *A61F 2250/0031* (2013.01); *A61F 2250/0059* (2013.01); *A61F 2250/0071* (2013.01); *A61F 2002/016* (2013.01); *A61F 2230/0023* (2013.01); *A61F 2230/006* (2013.01); *A61F 2230/0089* (2013.01)

(58) Field of Classification Search
CPC  A61F 2/01–2/013; A61F 2002/011–2002/018
USPC ......................................... 606/200; 623/1.11
See application file for complete search history.

(56) References Cited

U.S. PATENT DOCUMENTS

| | | | | |
|---|---|---|---|---|
| 5,683,411 A | * | 11/1997 | Kavteladze et al. | 606/200 |
| 6,214,025 B1 | * | 4/2001 | Thistle et al. | 606/200 |
| 6,241,746 B1 | * | 6/2001 | Bosma et al. | 606/200 |
| 6,582,447 B1 | * | 6/2003 | Patel et al. | 606/200 |
| 2002/0193825 A1 | * | 12/2002 | McGuckin et al. | 606/200 |
| 2003/0176888 A1 | * | 9/2003 | O'Connell | 606/200 |
| 2006/0036279 A1 | * | 2/2006 | Eidenschink et al. | 606/200 |
| 2008/0027481 A1 | * | 1/2008 | Gilson et al. | 606/200 |

FOREIGN PATENT DOCUMENTS

| | | |
|---|---|---|
| DE | 4030998 A | 10/1990 |
| EP | 0605276 A | 7/1994 |
| WO | WO 02/22048 A | 3/2002 |
| WO | WO 2006/107939 A1 | 10/2006 |
| WO | WO 2008/010197 A | 1/2008 |

* cited by examiner

*Primary Examiner* — Katherine Dowe
*Assistant Examiner* — Jonathan Hollm
(74) *Attorney, Agent, or Firm* — Brinks Gilson & Lione

(57) ABSTRACT

A filter unit (3) for inserting into a blood vessel (1) is disclosed, the filter unit (3) comprising: —a stent-like body (2) having a superior end (4) and a inferior end (5), the stent-like body (2) being able to expand in order to engage a wall of the blood vessel (1), —two cone-shaped units (6, 7) each having a base opening (8, 9) and a tip (10, 11), one base opening (8) being operatively connected to the superior end (4) of the stent-like body (2), the other base opening (9) being operatively connected to the inferior end (5) of the stent-like body (2), wherein the tips (10, 11) of the cone-shaped units (6, 7) point towards each other.

13 Claims, 3 Drawing Sheets

BLOOD FILTER

Figure 1:
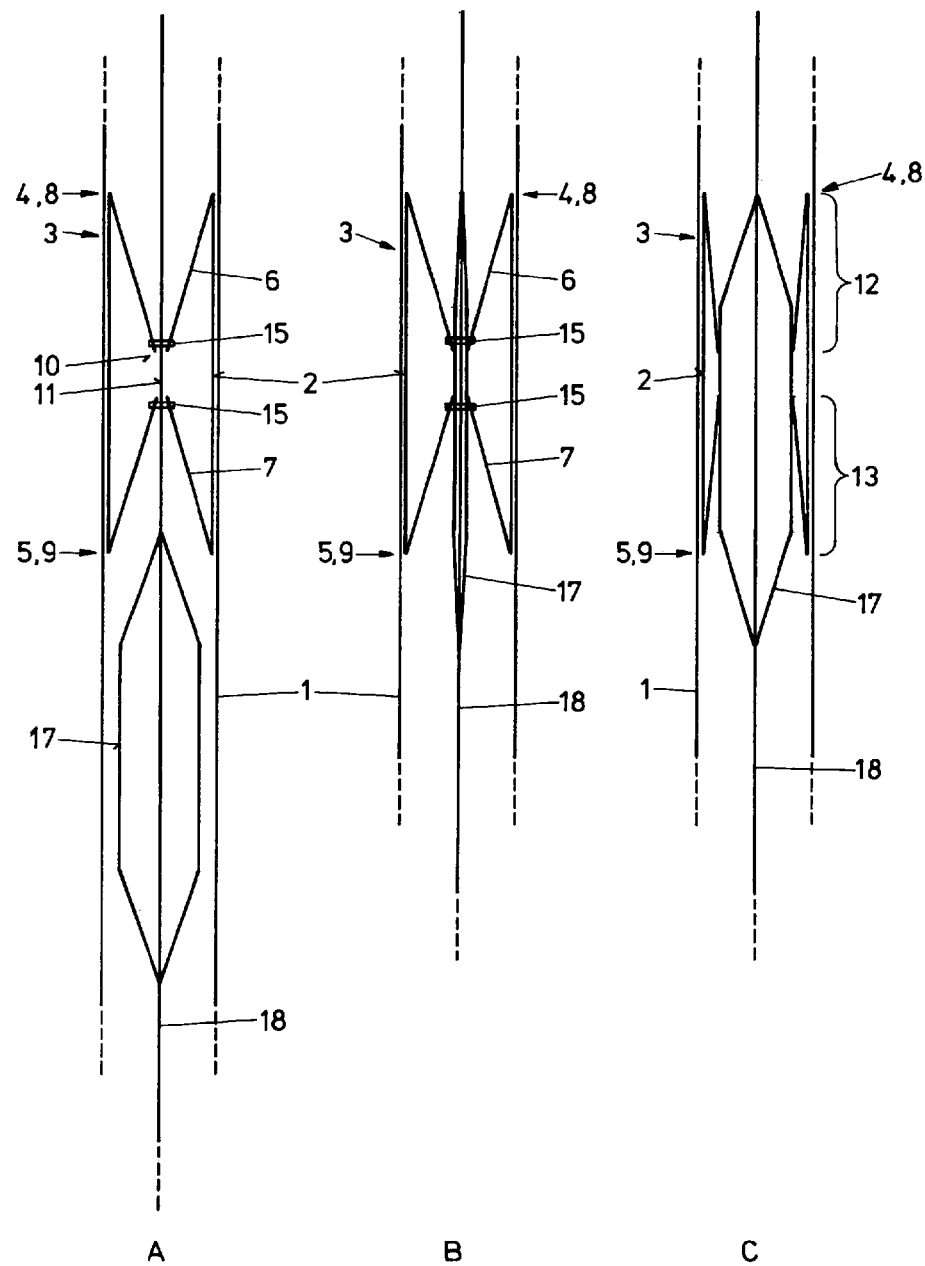

This application claims the benefit of priority to PCT/EP2008/061819 filed on Sep. 5, 2008 entitled "BLOOD FILTER," the entire contents of which are incorporated herein by reference.

The present invention is related to a filter unit for placement into a blood vessel that is operable to catch and retain embolic material.

Vena cava filters play an important role in the prevention of pulmonary embolism. The filters can trap clots flowing through the venous system before reaching the heart and lungs. They are easily placed using a percutaneous procedure generally from a femoral or jugular vein. The filters are usually place in the inferior vena cava (IVC) below the renal vein.

For many patients, the risk of embolism is short-term and limited to a definable period of time. Because of the long-term risks associated with implantation of a permanent blood filter, including venous stasis due to caval occlusion and its related complications, patients whose risk period is limited are not considered good candidates for permanent blood filters. Therefore, it has already been proposed to use a temporal blood filter. In this connection, reference is made to US-2003/0 176 888 A1 disclosing a vena cava filter with a bio-degradable retaining element that triggers an open, stent-like configuration once the retaining element is absorbed.

It has been shown that the known blood filters have the risk of tilting while they are deployed in a blood vessel. Tilting of a blood filter generally results in complications, and the blood filter must be retrieved again. In addition, it is important that the blood filter is correctly inserted into the introducer sheath system. A false deployment in an up-side-down position may lead to insufficient filtration and/or migration.

Therefore, it is one object of the present invention, to provide a filter unit that does not have the above-mentioned drawbacks.

This and other objects are reached by the features of claim 1. Further embodiments of the present inventions are given in further claims.

The present invention is directed to a filter unit for inserting into a blood vessel, the filter unit comprising:
- a stent-like body having a superior end and a inferior end, the stent-like body being able to expand in order to engage a wall of the blood vessel,
- two cone-shaped units each having a base opening and a tip, one base opening being operatively connected to the superior end of the stent-like body, the other base opening being operatively connected to the inferior end of the stent-like body, wherein the tips of the cone-shaped units point towards each other. The conal shape allows most efficient filtration. The symmetrical design allows placement from above and below, i.e. from a femoral and jugular approach.

Therefore, one filter unit model can be used for all applications.

Bedside placement of the filter unit according to the present invention is feasible because of the good self-centering of the filter unit, and the large cell design allowing the blood to flow through it at any position. Long side struts, i.e. the stent-like body, will prevent tilting into branch vessels. Covering the inflowing renal veins, for example, does not cause any harm. The term "large cell design" means that the cross-sectional area of an expanded stent-like body is larger than a typical inflowing vein and, therefore, the ostium of the vein is maximally covered by one strut of the stent-like body. The term "bedside placement" means the deployment of a filter unit without using an imaging apparatus.

In an embodiment of the present invention, the cone-shaped units are convertible into stent-like sections.

In a further embodiment of the present invention, the stent-like sections form part of the stent-like body, meaning that the stent-like section will line up with the stent-like body.

In a still further embodiment of the present invention, the cone-shaped units comprise a plurality of filter legs that are, at their first end, operatively connected in order to form the tips of the cone-shaped units, and that are, at their second end, connected to the inferior end or to the superior end, respectively, of the stent-like body.

In a still further embodiment of the present invention, the filter legs are releasable connected at the tip of the cone-shaped units by a connecting member. Therewith, filtration can be terminated if no longer needed.

In a still further embodiment of the present invention, the connecting member comprises a predefined breaking point.

In a still further embodiment of the present invention, the connecting member is destructible by a force applied to the connecting member via an expandable balloon.

In a still further embodiment of the present invention, the connecting member is made of a bio-degradable material.

In a still further embodiment of the present invention, the stent-like body is made of a bio-degradable material having a longer resolution time than the bio-degradable material of the connecting member.

In a still further embodiment of the present invention, the tips of the cone-shaped units comprise an opening for receiving a guiding member.

In a still further embodiment of the present invention, the openings of the cone-shaped units lie on a longitudinal axis of the blood vessel.

In a still further embodiment of the present invention, an expandable balloon is mounted on the guiding member.

In a further embodiment of the present invention, the overall length of the filter unit, i.e. the stent-like body, is longer than a diameter of a blood vessel into which the filter unit is to be deployed. More specifically, the overall length of the filter unit is a factor of 1.5 to 2.5 longer than the diameter of the blood vessel into which the filter unit is to be deployed. For example, if the blood vessel is the vena cava having a diameter in the range of 1.5 to 2.5 cm, a filter unit having a overall length of 4 cm can very well be used.

It is again pointed out that the stent-like body preferably is a radially expandable device in order that migration in the vessel is prevented. Typically, a fully expanded stent-like body to be inserted into the vena cava has a diameter of 3 to 4 cm. Therefore, when inserted into a vena cava having a diameter in the range of 1.5 to 2.5 cm, a sufficient radial force remains to prevent migration of the filter unit.

The present invention will be further described in the following by referring to drawings showing exemplified embodiments of the present invention.

Figure 2A:
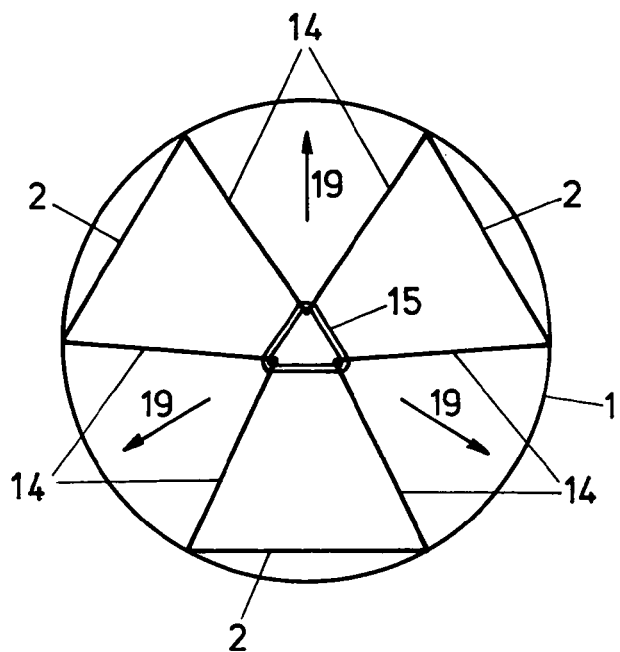
Figure 2B:
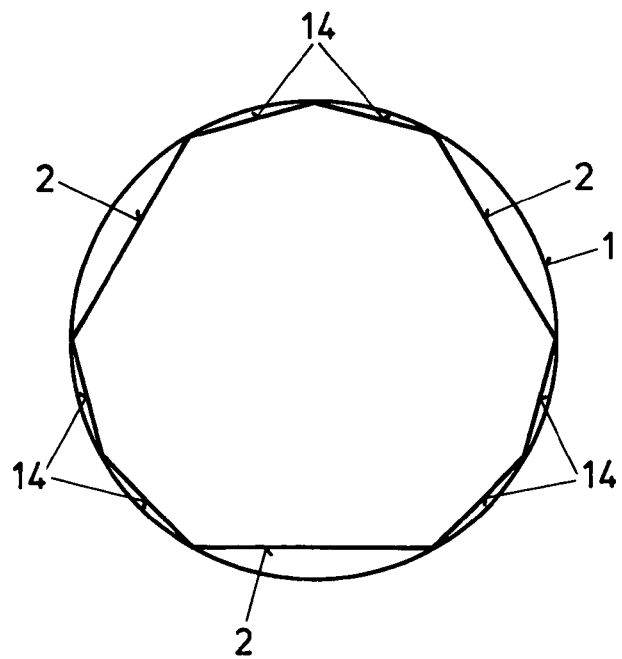
Figure 3:
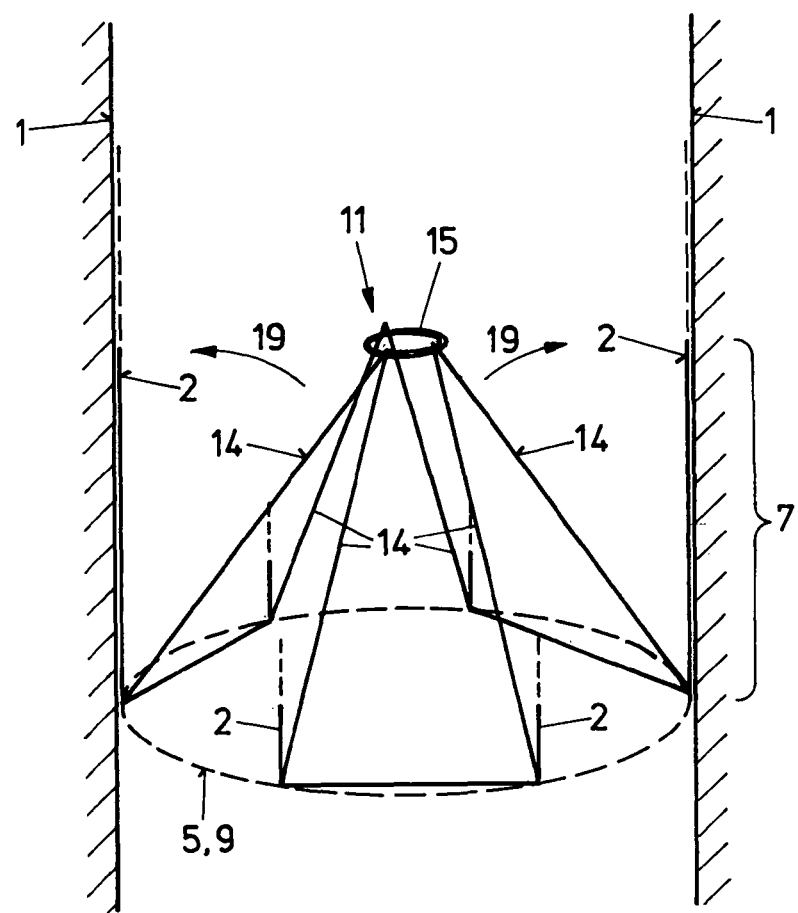

FIGS. 1A, 1B and 1C schematically show a blood vessel in a sectional view along a longitudinal axis, the blood vessel containing a filter unit according to the present invention, FIGS. 2A and 2B show the blood vessel of FIGS. 1A, 1B and 1C containing the filter unit in a cross sectional view, the filter unit being shown in FIG. 2A in a filtering configuration and in FIG. 2B in a open, stent-like configuration, and FIG. 3 shows a side view of a cone-shaped unit pertaining to the filter unit according to the present invention.

In FIG. 1A, a filter unit 3 according to the present invention is depicted, the filter unit 3 being employed in a blood vessel 1. The filter unit 3 comprises a stent-like body 2 and two cone-shaped units 6 and 7. The stent-like body 2 is in close contact with the inner wall of the blood vessel 1. This is achieved by using a preloaded or spring-like material for the stent-like body 2 forcing it towards the inner wall of the blood vessel 1. The possibility of a radial expansion of the stent-like body 2 is twofold important: First, the stent-like body 2 or the filter unit 3, respectively, can be folded and brought to a desired location by using commonly known coaxial introducer systems. Reference is made to U.S. Pat. No. 5,571,135.

Second, the radial expansion prevents the filter unit 3 from migrating, which can occur due to the blood flow through the corresponding blood vessel 1.

The stent-like body 2 has a superior end 4, to which a base opening 8 of one cone-shaped unit 6 is operatively connected. At the opposite side of the stent-like body 2, at an inferior end 5 of the stent-like body 2, a base opening 9 of the second cone-shaped unit 7 is operatively connected to the stent-like body 2. The stent-like body 2 and the cone-shaped units 6 and 7 are, for example, made of the same material, e.g. Nitinol or biodegradable polymer. According to the present invention, the tips of the two cone-shaped units 6 and 7 point towards each other. The inventive filter unit 3 allows a very efficient filtration and an easy handling due to its double-conal shape with the tips of the cones facing each other. This is particularly advantageous because the inventive filter unit 3 can be inserted into a blood vessel either way. Therefore, one model of filter units 3 can be used for all applications. In addition, the relatively long stent-like body 2 compared to the diameter of even the largest blood vessel 1 in human bodies will prevent tilting into a branch blood vessel.

In a further embodiment of the present invention, the cone-shaped units 6 and 7 are made of filter legs that are preloaded in order that the stent-like body 2 fully engages the inner wall of the blood vessel 1. Therewith, the filter legs, which are connected to the stent-like body 2 at the base opening 8, 9, force the stent-like body 2 towards the inner wall of the blood vessel 1. As long as the filter legs are connected to form tips 10 and 11, respectively, the filter unit 3 is ready to perform the filtration.

In a further embodiment of the present invention, the tips 10 and 11 are obtained by holding together the filter legs by a connecting member 15, which can be removed. By removing the connecting member 15, the cone-shaped units 6 and 7 are converted into stent-like sections 12 and 13, respectively, as it is shown in FIG. 10. As can be seen in FIG. 10, the stent-like sections 12 and 13 generally lie in parallel to a part of the stent-like body 2. This configuration is called open configuration of the filter unit 3.

The possibility of converting the cone-shaped units 6 and 7 into stent-like sections 12 and 13 can be implemented in different ways. Different implementations will be described later on in this specification.

Besides the structure and elements of the filter unit according to the present invention, FIGS. 1A, 1B and 1C also show how a deployed filter unit 3 can be converted into an open configuration by using an expandable balloon 17. In FIG. 1A, the expandable balloon 17, which is guided on a guiding member 18, e.g. a wire, to the position of the filter unit 3. In the vicinity of the filter unit 3, the expandable balloon 17 is inflated in order to center the guiding member 18 in the blood vessel 1. Due to the symmetrical structure of the filter unit 3 (and the cone-shaped units 6, 7), the guiding member 18—now centered by the expanded expandable balloon 17—will automatically be in line with the tips 10, 11 of the cone-shaped units 6, 7. The tips 10, 11 provide an opening 20 to receive the guiding member 18. As soon as the guiding member 18 is received by the opening 20, the expandable balloon 17 is deflated. As a result of the deflation of the expandable balloon 17, the guiding member 15 can be further advanced into the filter unit 3 until the deflated expandable balloon 17, which is attached to the guiding member 17, lies within the filter unit 3, as it is depicted in FIG. 1B.

By inflating the expandable balloon 17 in the filter unit 3, the connecting member 15 is broken up and removed from the tips 10, 11 of the cone-shaped units 6, 7. This is shown in FIG. 1C. In addition to the removal of the connecting member 15, filter legs forming the cone-shaped units 6, 7 are pushed towards the stent-like body 2 forming stent-like sections 12, 13. This is in particular important for those embodiments of the present invention that do not incorporate preloaded filter legs, i.e. filter legs which automatically will form stent-like sections 12, 13 as soon as the connecting member 15 is removed. After removing the expandable balloon 17 by retracting the guiding member 18, the filter unit 3 is in the open configuration, in which no filtration of blood takes place.

FIGS. 2A and 2B show a cross-sectional or top view of the blood vessel 1 containing the filter unit 3. While the filter unit 3 of FIG. 2A is in the filtering configuration, the filter unit 3 of FIG. 2B is in the open configuration, in which no filtering takes place.

The embodiment of FIG. 2A comprises a cone-shaped unit 6 or 7 with triangular elements that are preloaded and will expand in the direction indicated by reference sign 19 as soon as the connecting member 15 at the tip of the triangular elements (tip 10, 11 of the cone-shaped unit 6 or 7) is removed. The connecting member 15 forms an opening, through which the guiding member 18 as well as the expandable balloon 17 may pass, as it has been described in connection with FIGS. 1A, 1B and 1C.

As soon as the connecting member 15 is removed, the triangular elements of the cone-shaped units 6, 7 will pivot as indicated by the arrow 19, and the triangular elements will form stent-like sections 12, 13 (FIG. 1C). As a result, the open configuration of the filter unit 3—as it is depicted in FIG. 2B—is obtained.

FIG. 3 shows a side view of a part of the filter unit 3 that is inserted in a blood vessel 1 and that is in filtering configuration. In fact, only one of the two cone-shaped units is depicted in FIG. 3. In addition, the stent-like body 2 is only shown partially and is indicated by a dashed line to a limited extent. As in FIGS. 2A and 2B, the cone-shaped unit 7 of FIG. 3 is formed of triangular elements having its base on the base opening 9 of the cone-shaped unit 7. In order to more clearly indicate the position of the cone-shaped unit 7, a circumference of the blood vessel 1 is shown by a dashed line in the region of the base opening 9 of the cone-shaped unit 7.

For all of the above-mentioned embodiments of the present invention, the connecting member 15 can be implemented in many different ways:

In a first embodiment of the present invention, the connecting member 15 is made of a rigid, non-breakable material. Clearly, such an embodiment results in a non-convertible filter unit, i.e. the filter unit can only be used in the filtering configuration. A conversion into an open configuration is not planned. Such a filter unit 3 may be used for a permanent installation.

In a second embodiment of the present invention, the connecting member 15 comprises a predetermined breaking point. Therewith, filtration can be terminated if it is no longer desired. A breaking point may be, for example, a weak point in the connecting member 15. The breaking point will then be designed to break when a predetermined force applied to the connecting member 15 is exceeded. The predetermined force must be above the physiological sheer force of blood. For example, the predetermined force may be the result of a pressure of 10 mm Hg applied to the connecting member 15.

In a third embodiment of the present invention, the connecting member 15 is made of a suture holding together the filter legs 14 of the cone-shaped units. To convert the filter unit 3 from the filtration configuration into the open configuration, the suture is simply cut open. As a result thereof, the filter legs will extend to the inner wall of the blood vessel.

Alternatively, the suture is made of bio-degradable material with a fixed resolution time. Such an implementation is in particular advantageous for a temporal installation of a blood filter, as it is necessary for patients with temporal risk of pulmonary embolism, for example.

In a still further embodiment of the present invention, the entire filter unit is made of bio-degradable material. Such a filter unit can readily be used as temporal blood filter, without the need to actively retrieve the filter unit after is no longer needed. The inventive filter unit comprises a connecting member made of bio-degradable material, as the embodiment mentioned-above. Furthermore, at least the cone-shaped units are also made of bio-degradable material although the material for the cone-shaped units having a longer resolution time than for the material of the connecting member. Therewith, the connecting member is resolved earlier as the cone-shaped units.

In an even further embodiment of the present invention, the stent-like body is additionally made of bio-degradable material having a longer or an equal long absorption time than the material of the cone-shaped units. As a result thereof, the filter unit will completely be absorbed in two steps: First, the connecting member will be absorbed and the filter unit will be converted in the open configuration. Second, the remaining elements of the filter, namely the cone-shaped units as well as the stent-like body, will also be absorbed. Finally, the filter unit will completely disappear after a certain time without the need of a further intervention. Reasonable times for the absorption of the connecting member will be three to six months, and for the remaining elements twelve to eighteen months.

The invention claimed is:

1. A filter unit for inserting into a blood vessel, the blood vessel having a wall, the filter unit comprising:
a stent-like body having a superior end, an inferior end, and a plurality of superior linear members extending in a common radial plane, each superior linear member having a length and being adapted for engaging the wall of the blood vessel, the stent-like body being able to expand in order to engage the wall of the blood vessel; and
two cone-shaped units each having a base opening and a tip, one base opening having a superior circumference and being operatively connected to the superior end of the stent-like body, the other base opening being operatively connected to the inferior end of the stent-like body, wherein the sum of the lengths of the superior linear members is less than the superior circumference, wherein the cone-shaped units are formed from a plurality of triangular elements, each triangular element comprises a pair of filter legs and has a triangle base, wherein each filter leg is connected to one filter leg of the adjacent triangular element at the triangle base but not connected to any filter leg associated with the same triangular element at the triangle base, one of the filter legs of the pair having a tip connection to the other one of the filter legs of the pair at the tip, wherein the tip connections are the only connections between any two of the superior linear members;
wherein the triangle base is adapted for arrangement at a circumference of the blood vessel, wherein the tips of the cone-shaped units point towards each other.

2. The filter unit according to claim 1, wherein the cone-shaped units are convertible into stent-like sections.

3. The filter unit according to claim 2, wherein the stent-like sections form part of the stent-like body.

4. The filter unit according to claim 1, wherein the filter legs of the cone-shaped units are, at their first end, operatively connected in order to form the tips of the cone-shaped units, and that are, at their second end, connected to the inferior end or to the superior end, respectively, of the stent-like body.

5. The filter unit according to claim 4, wherein the filter legs are releasable connected at the tip of the cone-shaped units by a connecting member.

6. The filter unit according to claim 5, wherein the connecting member comprises a predefined breaking point.

7. The filter unit according to claim 5, wherein the connecting member is destructible by a force applied to the connecting member via an expandable balloon.

8. The filter unit according to claim 5, wherein the connecting member is made of a bio-degradable material.

9. The filter unit according to claim 8, wherein the stent-like body is made of a bio-degradable material having a longer resolution time than the bio-degradable material of the connecting member.

10. The filter unit according to claim 1, wherein the tips of the cone-shaped units comprise an opening for receiving a guiding member.

11. The filter unit according to claim 10, wherein the openings of the cone-shaped units are configured to lie on a longitudinal axis of the blood vessel.

12. The filter unit according to claim 10, wherein the openings of the cone-shaped units can fit an expandable balloon that is mounted on the guiding member.

13. The filter unit according to claim 1, wherein an overall length of the stent-like body is configured to be longer than a diameter of a blood vessel into which the stent-like body is to be deployed.

* * * * *